United States Patent [19]

Marzoni

[11] Patent Number: 4,734,501

[45] Date of Patent: Mar. 29, 1988

[54] N-ALKYLATION OF DIHYDROLYSERGIC ACID

[75] Inventor: Gifford P. Marzoni, Indianapolis, Ind.

[73] Assignee: Eli Lilly and Company, Indianapolis, Ind.

[21] Appl. No.: 782,339

[22] Filed: Oct. 1, 1985

[51] Int. Cl.$^4$ ............................................. C07D 457/04
[52] U.S. Cl. ........................................ 546/69; 546/67; 546/68
[58] Field of Search ............................. 546/67, 68, 69

[56] References Cited

U.S. PATENT DOCUMENTS 3,183,234  5/1965  Garbrecht et al. ............. 260/285.5
3,580,916  5/1971  Garbrecht et al. ............. 260/285.5

OTHER PUBLICATIONS

Khromov-Borisov et al., "p,p*-Bis(quaternary-p-terphenylammonium) salts", *Chem. Abst.* 88:62132v (1978).

Schneider et al., "N-Alkylated Aromatic Amines", *Chem. Abst.* 92:22227f (1980).

Hu et al., "New Method for Synthesis of N-Phenyl-N'-Isopropylphenyldiamine", *Chem. Abst.* 100:67912a (1983).

Frehel et al., "1,2,3,6,7,10B-Hexahydrothieno (3',2': 03,4)pyrido[1,2-a]pyrazin-4-ones", *Chem. Abst.* 101:151882u (1984).

Lipshutz et al. in *J. Am. Chem. Soc.* 103, 7672-7674 (1981).

Veeravagu et al. in *J. Am. Chem. Soc.* 86, 3072-3075 (1964).

Cardillo et al. in *Tetrahedron*, vol. 23, 3771-3783 (1967).

Kikugawa et al. in *Synthesis*, 461-462 (1981).

Plieninger in *Chem. Ber.* 87, 127-128 (1954).

Shirley et al. in *J. Am. Chem. Soc.* 75, 375-378 (1953).

Smidrkal et al., *Collect. Czech. Chem. Commun.*, 47, 622 (1982).

*Primary Examiner*—Donald G. Daus
*Assistant Examiner*—Cecilia Shen
*Attorney, Agent, or Firm*—Edward P. Gray; Leroy Whitaker

[57] ABSTRACT

The present invention provides a process for N-alkylating dihydrolysergic acid with a substituted benzenesulfonate derivative.

5 Claims, No Drawings

N-ALKYLATION OF DIHYDROLYSERGIC ACID

BACKGROUND OF THE INVENTION

The standard procedure commonly used by synthetic organic chemists to alkylate indoles requires the use of an alkyl halide under normal alkylation procedures. However, this procedure works only for lower alkyl groups which exhibit little or no steric hindrance. As the alkyl halides become more substituted or sterically hindered, elimination to the olefin becomes the prevalent reaction, and in many cases is the predominent reaction. See, e.g., Lipshutz et al. in *J. Am. Chem. Soc.* 103, 7672–7674 (1981) and Veeravagu et al. in *J. Am. Chem. Soc.* 86, 3072–3075 (1964).

A variety of methods exist for alkylating the nitrogen atom of indole. Cardillo et al. in *Tetrahedron*, Vol. 23, 3771–3783 (1967) and Kikugawa et al. in *Synthesis* 461–462 (1981) disclose the N-alkylation of indoles with various halide derivatives. Plieninger in *Chem. Ber.* 87, 127–128 (1954) disclose the alkylation of indole with benzyl chloride and benzyl p-toluenesulfonate. Shirley et al. in *J. Am. Chem. Soc.* 75, 375–378 (1953) disclose the synthesis of 1-methylindole by reacting indole with methyl p-toluenesulfonate. These processes do not relate to more complex substrates or substituents which are prone to elimination.

Procedures for alkylating ergolines with alkyl halides or sulfates are known. U.S. Pat. Nos. 3,183,234 and 3,580,916 disclose a procedure for alkylating dihydrolysergic acid in liquid ammonia in the presence of sodium amide and the alkylating agent. This procedure provides the desired product in lower yield less reproducibly than the process disclosed herein.

The present process permits the alkylation of the nitrogen atom at the 1-position of dihydrolysergic acid with a sterically hindered alkyl group employing substituted benzenesulfonate. The use of substituted benzenesulfonate reduces the rate of the competing elimination reaction which produces the undesired olefinic derivative.

SUMMARY OF THE INVENTION

The present invention provides a process for alkylating the nitrogen atom at the 1-position of dihydrolysergic acid. More specifically, this invention relates to a process for preparing a compound of the formula

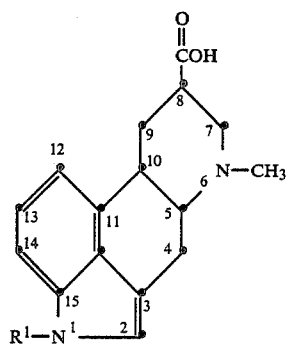

wherein $R^1$ is $C_3$–$C_8$ alkyl, —$CH_2C_2$—$C_4$ alkenyl, propargyl, $C_3$–$C_8$ cycloalkyl or $C_1$–$C_5$ alkyl substituted $C_3$–$C_8$ cycloalkyl, comprising treating a compound of the formula

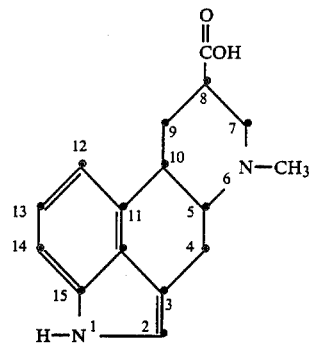

a substituted benzenesulfonate of the formula

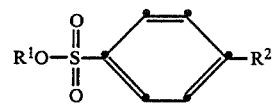

wherein $R^1$ is as defined above and $R^2$ is hydrogen, bromo, methyl or nitro, in the presence of a suitable base and solvent.

DETAILED DESCRIPTION OF THE INVENTION

In the above formula, the term "$C_3$–$C_8$ alkyl" represents a straight or branched primary or secondary alkyl chain having from three to eight carbon atoms. Examples of $C_3$–$C_8$ alkyl groups include n-propyl, isopropyl, n-butyl, sec.-butyl, n-pentyl, sec.-hexyl, n-heptyl, isooctyl and the like.

The term —$CH_2C_2$—$C_4$ alkenyl represents a straight or branched primary or secondary alkenyl group having at least one carbon-carbon double bond. Typical —$CH_2C_2$—$C_4$ alkenyl groups include allyl, 2-butenyl, 2-pentenyl and the like.

$C_3$–$C_8$ cycloalkyl represents cyclopropyl, cyclobutyl, cyclopentyl, cyclohexyl, cycloheptyl and cyclooctyl.

$C_1$–$C_5$ Alkyl substituted $C_3$–$C_8$ cycloalkyl represents a $C_3$–$C_8$ cycloalkyl group having one or more primary or secondary alkyl groups affixed thereto with one to five carbon atoms. Typical members of this classification include 2-methylcyclopropyl, 1-cyclopropylmethyl 2-methylcyclobutyl, 2,3-dimethylcyclopentylmethyl, 2,5-diethylcyclooctyl and the like.

While all aspects of the present process are believed operable, the present invention does have preferred aspects. Preferably, $R^1$ is $C_3$–$C_8$ alkyl, and especially isopropyl, and $R^2$ is methyl. Other preferred aspects of the present process will be noted hereinafter.

The process of the present invention relates to the N-alkylation of the nitrogen atom at the 1-position of dihydrolysergic acid with a benzenesulfonate derivative in the presence of a suitable base and a suitable solvent.

A variety of suitable bases may be employed in the present process. Preferred bases are the alkali metal hydroxides such as lithium hydroxide, sodium hydroxide and especially potassium hydroxide. The base will typically be present in the reaction mixture from about equimolar quantities of the base to the starting substrate to about ten or more molar equivalents of base for each molar equivalent of starting substrate. The preferred amount of base present in the reaction mixture will be from about two to about seven molar equivalents of base for each molar equivalent of starting substrate.

A benzenesulfonate derivative will also be employed in the present process. This compound will be present in the reaction mixture in an amount from about 1.0 molar equivalents to about 3.0 molar equivalents for each molar equivalent of starting substrate, more preferably from about 1.2 to about 2.0 molar equivalents of alkylating reagent for about each molar equivalent of starting material, and especially 1.5 molar equivalents.

A variety of suitable solvents may be employed in the present process. These solvents should be aprotic in nature and include N,N-dimethylformamide (DMF), dimethylsulfoxide (DMSO) or tetrahydrofuran (THF). The concentration of the starting material in the solvent is not critical, but it is preferred to employ a sufficient amount of solvent to keep the starting material in solution, or a slight excess. Large volumes of solvent are not necessary or desirable in the process.

The present process is substantially complete after about 12 hours to about 24 hours when conducted at a temperature in the range of about 15° C. to about 100° C., more preferably from about 20° C. to about 40° C.

Once the process of the present invention is complete, the product may be isolated according to standard procedures. Typically, water is added to the reaction mixture. The mixture may then be washed with a water immiscible organic solvent, such as methylene chloride or ethyl acetate, or filtered, and the pH of the aqueous phase is adjusted to approximately 6 with an acid, such as acetic acid or hydrochloric acid. The aqueous phase is then usually cooled to aid precipitation of the solid, and the precipitated solid is collected, typically by vacuum filtration. The product thus isolated may then be further purified by standard techniques, if desired, such as recrystallization from common solvents, like methanol or ethyl acetate, or chromatography over solid supports such as silica gel or alumina.

The present process has been found to produce N-substituted dihydrolysergic acid derivatives in high yields and to provide the product consistently in high purity, so that the compound may be used in the preparation of biologically active compounds without additional expensive purification steps.

The compounds prepared by the present process are preferably used as intermediates in the synthesis of a variety of compounds, for example, pharmaceuticals useful for the treatment of a variety of human disorders. The compounds are preferably used as intermediates to trans dihydrolysergic acid esters which block $5HT_2$ receptors without affecting alpha receptors, and are thus highly selective in their action. These compounds are potentially useful in treating disease states in which an excess of circulating serotonin is a major contributing cause. These disease states include hypertension, anorexia nervosa, depression, mania, carcinoid syndrome, migraine and vasospasm. For parenteral administration, the drug is dissolved in an isotonic salt solution and administered by the i.v. route. For oral administration, the drug is mixed with standard pharmaceutical excipients such as starch and loaded into capsules or made into tablets, each containing 0.1 to 100 mg of active drug. Dosage levels of from 0.1–10 mg/kg have been found to be effective in blocking $5HT_2$ receptors. Thus, the oral dosage would be administered 2–4 times per day, giving a daily dosage range of about 0.003 to about 10.0 mg/kg per day.

The biologically active compounds prepared from the compounds derived from the present process are disclosed in copending applications Ser. Nos. 782,340, 782,338, 782,342, 782,341, and Ser. No. 782,337, all filed even date herewith and incorporated herein by reference.

The compounds used as starting materials in the present process are known and readily prepared by procedures well known to those of ordinary skill in the art. 9,10-Dihydrolysergic acid is a known compound. The benzenesulfonate derivatives are either commercially available or readily prepared by standard procedures well known in the art. See, e.g., Edgell et al. in *Journal of the American Chemical Society* 77, 4899–4902 (1955) and *Organic Synthesis* Collective Volume 3, 366–367.

The following Examples further illustrate the process of the present invention. The Examples are not intended to be limiting to the scope of the invention in any respect and should not be so construed.

EXAMPLE 1

Synthesis of 1-(1-ethylpropyl)-6-methyl-ergoline-8-carboxylic acid.

To a 50 ml, three-neck round bottom flask was added 1.0 g (3.4 mmol) of 92% pure 9,10-dihydrolysergic acid, 1.03 g (15.8 mmol) of 86% pure powdered potassium hydroxide and 15 ml of DMF. This mixture was agitated until the solids were dissolved, and 1.79 g (7.4 mmol) of p-toluenesulfonic acid, 1-ethylpropyl ester was added. The reaction mixture was stirred for 19 hours at room temperature, and 35 ml of water was added. The reaction mixture was washed into a 250 ml erlenmeyer flask with deionized water, and the mixture was washed with 50 ml of methylene chloride. The aqueous layer was separated, saturated with an aqueous sodium chloride solution and washed with methylene chloride. The emulsified aqueous layer and the second organic layer were combined and the pH was adjusted to 6. The organic layer was separated and filtered by vacuum filtration. The resulting solid was washed with methylene chloride and dried in vacuo to provide 0.66 g of the title compound. The purity of the solid was 96.8% as determined by high performance liquid chromatography (HPLC). mp =187°–189° C. Exact mass: theory 341.22290; found 341.22261.

EXAMPLE 2

Synthesis of 1-(1-ethylpropyl)-6-methylergoline-8-carboxylic acid.

A 250 ml, three-neck round bottom flask was charged with 10.0 g (33.9 mmol) of 92% pure 9,10-dihydrolysergic acid, 10.3 g (158 mmol) of 86% pure powdered potassium hydroxide and 75 ml of DMF. The mixture was stirred until the solid constituents were completely dissolved, and 17.9 g (73.9 mmol) of p-toluenesulfonic acid, 1-ethylpropyl ester was added. The reaction mixture was stirred at room temperature overnight and 300 ml of deionized water was added. The mixture was filtered, and 1N hydrochloric acid was added to the filtrate until the pH was adjusted to approximately 6.5. The precipitated solid was collected by vacuum filtration and rinsed with water to provide 6.9 g of 1-(1-ethylpropyl)-6-methylergoline-8-carboxylic acid. The identity of the solid was determined by thin layer chromatography employing chloroform:methanol:acetic acid (18:6:1, v:v:v) as the solvent system as compared to an authentic reference standard. The products obtained from Example 1 and Example 2 were combined to provide 7.6 g of solid, which was recrystallized from methanol to provide 2.1 g of the desired product following drying of the solid in vacuo. The purity of the product was 95.6% as determined by HPLC as compared to an authentic reference standard.

EXAMPLE 3

Synthesis of (8β)-1-(cyclopropylmethyl)-6-methylergoline-8-carboxylic acid.

To a 50 ml, three-neck round bottom flask was added 1.0 g (3.39 mmol) of 92% pure 9,10-dihydrolysergic acid, 1.2 g (18.5 mmol) of 86% pure powdered potassium hydroxide and 15 ml of DMSO. The reaction mixture was stirred until all the solid ingredients had dissolved and 1.0 g (4.43 mmol) of p-toluenesulfonic acid, cyclopropylmethyl propylmethyl ester was added. The reaction mixture was stirred for 22 hours at room temperature and poured into 200 ml of ice water. The resulting solution was washed with 50 ml of ethyl acetate and the aqueous phase was acidified with glacial acetic acid. The resulting solid was collected by vacuum filtration, washed with water and dried in vacuo to provide 0.71 g of the title compound having a purity of 98.4% by HPLC. Exact mass: theory 324.1838; found 324.1834.

EXAMPLE 4

Synthesis of 1-(1-methylethyl)-6-methylergoline-8-carboxylic acid

To a 250 ml, three-neck round bottom flask was added 15.0 g (50.8 mmol) of 92% pure 9,10-dihydrolysergic acid, 18.08 g (277.7 mmol) of 86% pure powdered potassium hydroxide and 150 ml of DMSO. The mixture was stirred for approximately 15 minutes and 14.3 g (66.8 mmol) of p-toluenesulfonic acid, 1-methylethyl ester was added dropwise to the reaction mixture over a period of about 10 minutes. The reaction mixture was stirred at room temperature for approximately 24 hours and poured into 750 ml of ice water. The mixture was washed with 150 ml of ethyl acetate, and the aqueous phase was separated and the pH was adjusted to 5 with glacial acetic acid. The mixture was cooled in the freezer and the precipitated solid was collected by vacuum filtration. The solid was washed with water and dried in vacuo to provide 12.8 g of the title compound. A second crop of 0.82 g of the desired compound was obtained. The purity of the first crop material was 99.6% and the purity of the second crop material was 98.8% as determined by HPLC. Exact mass: theory 312.18378; found 312.18485.

EXAMPLE 5

Synthesis of 1-(1-ethylpropyl)-6-methylergoline-8-carboxylic acid

A 500 ml, three-neck round bottom flask was charged with 11.72 g (180.0 mmol) of 86% pure powdered potassium hydroxide, 10.0 g (33.9 mmol) of 92% pure 9,10-dihydrolysergic acid and 150 ml of DMSO. The mixture was stirred at room temperature for 15 minutes, and 10.3 g (42.6 mmol) of p-toluenesulfonic acid, 1-ethylpropyl ester was added. The mixture was stirred at room temperature for 19 hours, and 1000 ml of ice water was added. The mixture was washed twice with 250 ml aliquots of ethyl acetate, and the pH of the aqueous layer was adjusted to 5 with glacial acetic acid. The mixture was cooled and the precipitated solid was collected by vacuum filtration. The solid was dried under vacuum to provide 7.94 g of 1-(1-ethylpropyl)-6-methylergoline-8carboxylic acid. A second crop of material was obtained to provide 0.9 g of product. The purity of the first crop was 96.7%, and the purity of the second crop was 96%. Total yield 72.1%. The identity of the product was determined by thin layer chromatography as compared to an authentic reference standard.

EXAMPLE 6

Synthesis of 1-cyclopentyl-6-methylergoline-8-carboxylic acid

To a 500 ml, three-neck round bottom flask was added 10.0 g (33.9 mmol) of 92% pure 9,10-dihydrolysergic acid, 11.72 g (180.0 mmol) of 86% pure powdered potassium hydroxide and 150 ml of DMSO. The mixture was stirred for 15 minutes and 10.22 g (42.6 mmol) of p-toluenesulfonic acid, cyclopentyl ester was added. The mixture was stirred at room temperature for about 20 hours and an additional 3.11 g (13.0 mmol) of p-toluenesulfonic acid, cyclopentyl ester was added. The mixture was stirred for an additional two hours and was poured into 750 ml of ice water. The mixture was washed twice with 200 ml portions of ethyl acetate and the pH of the aqueous phase was lowered to about 5 with glacial acetic acid. The mixture was cooled and the precipitated solid was collected by vacuum filtration. The solid was washed with water and dried under vacuum to provide 10.05 g of the title compound having a purity of 96.3%. Yield 85.2%. Exact mass: theory 339.20725; found 339.20633.

I claim:

1. A process for preparing a compound of the formula

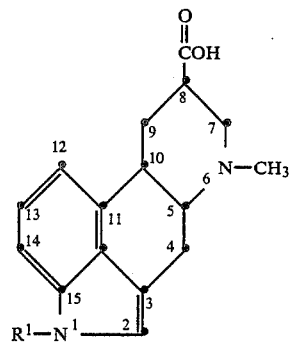

wherein $R^1$ is $C_3$–$C_8$ alkyl, —$CH_2C_2$—$C_4$ alkenyl, propargyl, $C_3$–$C_8$ cycloalkyl or $C_1$–$C_5$ alkyl substituted $C_3$–$C_8$ cycloalkyl, comprising treating a compound of the formula

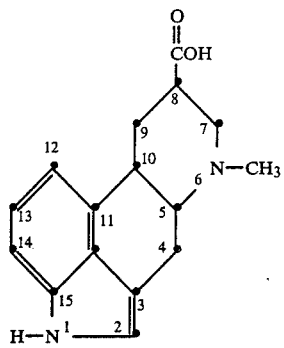

with a substituted benzenesulfonate of the formula

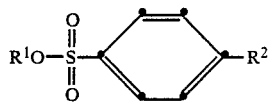

wherein $R^1$ is as defined above and $R^2$ is methyl in the presence of a suitable alkali metal hydroxide base and solvent.

2. A process of claim 1 wherein the suitable base is potassium hydroxide.

3. A process of claim 1 wherein $R^1$ is $C_3$–$C_8$ alkyl.

4. A process of claim 3 wherein the $C_3$–$C_8$ alkyl group is isopropyl.

5. A process of claim 1 wherein $R^2$ is methyl.

* * * * *